United States Patent [19]

Chamberlin, Sr.

[11] Patent Number: Plant 7,012

[45] Date of Patent: Sep. 5, 1989

[54] NECTARINE TREE, HARVEST SUN

[75] Inventor: Thomas O. Chamberlin, Sr., Visalia, Calif.

[73] Assignees: Metzler Investments; Metropolitan Life Insurance Company, both of Del Rey, Calif.

[21] Appl. No.: 261,401

[22] Filed: Oct. 24, 1988

[51] Int. Cl.[4] ..... A01H 5/00
[52] U.S. Cl. ..... Plt./41
[58] Field of Search ..... Plt./41

*Primary Examiner*—Robert E. Bagwill
*Attorney, Agent, or Firm*—Worrel & Worrel

[57] ABSTRACT

A new and distinct variety of nectarine tree denominated varietally as "Harvest Sun" and which is somewhat similar in its date of harvesting with the fruit produced by the Ito et al. nectarine tree (U.S. Plant Pat. No. 4,518) but which is distinguished therefrom and characterized principally as to novelty by producing freestone fruit which have an attractive skin color and a yellow colored flesh, the subject variety maturing for commercial harvesting and shipment approximately August 20 through August 25 in the San Joaquin Valley of Central California.

1 Drawing Sheet

BACKGROUND OF THE NEW VARIETY

The present invention relates to a nectarine tree, designated varietally by the name "Harvest Sun", and more particularly to a nectarine tree which bears an attractively colored fruit which ripens for commercial harvesting and shipment approximately at the same time of the season as the Ito Nectarine Tree (U.S. Plant Pat. No. 4,518), but which is distinguished therefrom in bearing fruit which have a pleasing substantially globose shape, a crisp flesh texture, and an excellent flavor.

For decades the applicant has grown large acreages of fruit trees for his employer the H. P. Metzler & Sons company of Del Rey, Calif., and has further constantly sought to produce improved varieties thereof. One of the several procedures utilized by the inventor to produce new fruit trees has been to germinate large numbers of seeds of unknown parentage, grow the resulting seedlings to maturity, and then evaluate the resultant trees and the fruit produced thereby. The subject variety of Nectarine Tree, "Harvest Sun" is a product of the above-identified procedure. More particularly, the subject variety of Nectarine Tree was originated from seed that was collected from the applicant's employer's Nursery No. 13 which is located at 5286 South Del Rey Ave. in Del Rey, Calif. The seed, which was collected in 1977, was planted in the applicant's employer's same nursery at Del Rey, Calif. The seedling of the present variety was germinated by the applicant and grown with thousands of other seedlings on this same ranch until its unique qualities were detected and appreciated.

ORIGIN AND ASEXUAL REPRODUCTION OF THE NEW VARIETY

After detecting the unique characteristics of the newly found seedling, the applicant asexually reproduced the new variety, in 1980, by removing buds from the parent tree and by budding them into test trees which were growing in the H. P. Metzler & Sons test plot which is located at 5286 South Del Rey Avenue in Del Rey, Calif. These test trees, which were budded in early spring of 1981 produced their first fruit in 1982. In the years which followed, the applicant studied the trees' characteristics, including the fruit produced thereby, to determine whether the characteristics observed in the original seedling were present. The budded test trees were grown at the designated ranch until it was subsequently determined that the new variety of nectarine tree dependably and accurately reproduced the superior characteristics observed by the applicant in the original seedling. The instant variety of nectarine tree is somewhat similar in its date of harvest to the Ito, et al. nectarine tree (U.S. Plant Pat. No. 4,518), however, the present variety of nectarine tree is distinguishable therefrom inasmuch as it produces fruit which are freestone by nature, in contrast to the Ito, et al. U.S. Plant Pat. No. 4,518 which produces a clingstone fruit, and in addition the fruit of the subject variety has a pleasing, round shape, appears to be more richly colored, and has a pleasing low acid taste.

BRIEF DESCRIPTION OF THE DRAWINGS

The accompanying drawing is a color photograph of a characteristic twig bearing typical leaves, several nectarines showing their external coloration sufficient matured for harvesting and shipment, a nectarine severed in the axial plane to illustrate the flesh and stone characteristics, all of the subject variety.

DETAILED DESCRIPTION

Referring more specifically to the pomological details of this new and distinct variety of nectarine tree, the following has been observed under the ecological conditions prevailing at the designated orchard near Del Rey, Calif. All major color code designations are by reference to the Inter-Society Color Council, National Bureau of Standards. Common descriptive color names are also employed occasionally.

Tree:

*Size.*—Generally — Average.

*Vigor.*—Very vigorous.

*Form.*—Average, depending upon pruning practices.

*Productivity.*—Considered very good.

*Regularity of bearing.*—Good, the nectarine variety "Harvest Sun" has produced a good crop during each year it was observed.

Trunk:

*Size.*—Average.

*Surface Texture.*—Average as compared with other nectarine cultivars which grow in the same geographical area.

*Surface texture.*—Color — Grey-brown, (80 gy. y. Br).

*Lenticels.*—Numbers — Approximately 10 lenticels per square inch were observed.

*Lenticels.*—Color — Yellow-brown, (76 l. y. Br).

Branches:

*Size.*—Considered average as compared with other nectarine cultivars.

*Surface texture.*—Average, and appearing quite similar to the trunk.

*Bark.*—Color — Grey-brown, (80 gy. y. Br).

*Lenticels.*—Size — Considered large. Numbers — Approximately 10 lenticels per square inch were observed. Color — Yellow-brown (76 l. y. Br).

LEAVES

Size:

*Average length.*—7 to 8 inches, (177.8 mm.-203.2 mm.).

*Average width.*—2 to 2¼", (50.8 mm.-57.15 mm.).

*Shape.*—Generally — Lanceolate.

*Color.*—Upwardly Disposed Surface — Bright green, (137 d.y. G). Downwardly Disposed Surface — Dark green, (125 m. Ol G).

*Marginal form.*—Generally — Crenate.

*Base.*—Form — Acute.

*Petiole.*—Average Length — Approximately ½", (12.7 mm.). Caliper — Approximately 1/16", (1.588 mm.).

*Stem Glands.*—Numbers — Generally one pair of stem glands are evident. Arrangement — The pair of stem glands are located at the base of the leaf. Size — Considered small as compared with other nectarine cultivars, approximately 1/32", (0.794 mm.). Color — Light green, (136 m. y. G). Form — Considered reniform.

FLOWER BUDS

Generally: The characteristics of the buds were observed during that early phase of its development when the buds first showed signs of red coloration.

*Shape.*—Generally — Rounded in appearance.

*Average length.*—Approximately ¼", (6.35 mm.).

*Average width.*—Approximately ¼", (6.35 mm.).

*Color.*—Dark Red, (17 v.d. red). The bud color is somewhat slightly different as compared with the buds produced by other common nectarine cultivars growing in the same geographical area.

FLOWERS

Date of bloom: In 1988, the date of bloom was approximately February 25 through March 3 at Del Rey, Calif.

*Flowers.*—Generally — The variety "Harvest Sun" produces a relatively large showy light pink blossom, however the flowers are generally considered average in appearance with respect to other common nectarine cultivars which bloom at approximately the same time of the season.

*Petals.*—Size — Average.

*Average length.*—Approximately 13/16", (20.638 mm.).

*Average width.*—Approximately 11/16", (17.462 mm.).

*Petals.*—Shape — The petals appear slightly elongated. Color — Light pink, (252 p. p. pink). The petals may have a slightly darker pink color at the base thereof, (249 l p. pk).

Fruit:

*Maturity when described.*—In 1988, the variety "Harvest Sun" was ripe for commercial and harvesting and shipment approximately August 20 through August 25 at Del Rey, Calif.

*Uniformity.*—Average as compared with other nectarine cultivars.

*Average axial diameter.*—Approximately 2¾"-3", (69.84 mm.-76.2 mm.).

*Average diameter transverse in the suture plane-*.—Approximately 2¾", (69.85 mm.).

*Average diameter transverse and at right angles to the suture plane.*—Approximately 2¾"-3", (69.85 mm.-76.2 mm.).

*Form.*—Uniformity — Good.

*Symmetry.*—Symmetrical.

*Suture.*—Generally — The suture appears as a very smooth distinct line which extends from the base to the apex. As a general matter, the suture blends in quite well with the skin color. Length — Approximately 3¼", (82.55 mm.).

*Ventral surface.*—Shape — Rounded.

*Stem cavity.*—Depth — Approximately 7/16", (11.12 mm.). Shape — Rounded.

*Base.*—Width — Average.

*Apex.*—Shape — Appearing somewhat slightly rounded and occasionally almost flat.

*Pistil point.*—Shape — Small and generally receded.

*Stem.*—Length — Approximately 5/16", (7.938 mm.). Caliper — Approximately ⅛", (3.175 mm.).

*Skin.*—Thickness — Considered average as compared with other nectarine cultivars.

*Surface texture.*—Glabrous.

*Tenacious to flesh.*—Yes.

*Tendency to crack.*—Not observed.

*Color.*—Approximately 75% of the skin surface is colored red, (13 deep red). The remaining surface area is colored yellow, (83 brill. y.).

*Flesh color.*—Generally — Light yellow, (83 brill. y.).

*Surface of pit cavity.*—Surface texture — Rough.

*Color of pit cavity.*—Variable, dark red and occasionally yellow, (14 v. deep red) and (83 brill. y.).

*Juice production.*—Juicy.

*Flavor.*—Mild and having a low acid taste.

*Aroma.*—Slight yet pleasant.

*Taste.*—Good.

*Fibers.*—Not evident.

*Ripening.*—Even.

*Eating quality.*—Crisp and having a good flavor.

Stone:

*Attachment.*—The stone of the subject variety is held very tightly in the pit cavity and appears upon first examination to be a clingstone, however, at commercial maturity the stone will break free making it most correctly, a freestone fruit.

*Fibers.*—Not evident.

*Size.*—Generally — Average.

*Average length.*—Approximately 1½", (38.1 mm.).

*Average width.*—Approximately ⅞", (22.225 mm.).

*Average thickness.*—Approximately ¾", (19.050 mm.).

*Form.*—Generally — Oval.

*Base.*—Shape — Slightly elongated and appearing nearly flat.

*Apex point.*—Shape — Very small.

*Sides.*—Surface Texture — Quite rough.

*Ridges.*—Generally — Approximately 1/16" in height, (1.588 mm.). Further the ridges appear almost cup-shaped.

*Stone.*—Color — Stained dark red, (17 v. d. red).

*Tendency to split.*—Not observed.

Fruit use: Fresh market type nectarine for both local and long distance markets.

Storage quality: Noteworthy. The subject variety has been held in cold storage for periods in excess of three weeks with no deleterious effects noted.

Shipping quality: Noteworthy, the variety has a firm crisp flesh at commercial maturity. The variety otherwise handles and ships quite well under normal conditions.

Although the new variety of nectarine tree possesses the described characteristics as a result of the growing conditions prevailing in Del Rey, Calif., in the Central part of the San Joaquin Valley of Central California, it is to be understood that variations in the usual magnitude and characteristics incident to growing conditions, fertilization, pruning and pest control are to be expected.

Having thus described and illustrated my new variety of nectarine tree, what I claim:

1. A new and distinct variety of nectarine tree to be denominated varietally as "Harvest Sun" substantially as illustrated and described and which is characterized principally as to novelty by its production of fruit which are somewhat similar in their date of harvesting with the fruit produced by the Ito et al. nectarine tree, (U.S. Plant Pat. No. 4,518), but which is distinguished therefrom by producing fruit which are freestone by nature, have a pleasing globose shape, and an attractive skin color, the fruit of the subject variety ripe for commercial harvesting and shipment approximately August 20 through 25 in the San Joaquin Valley of Central California.

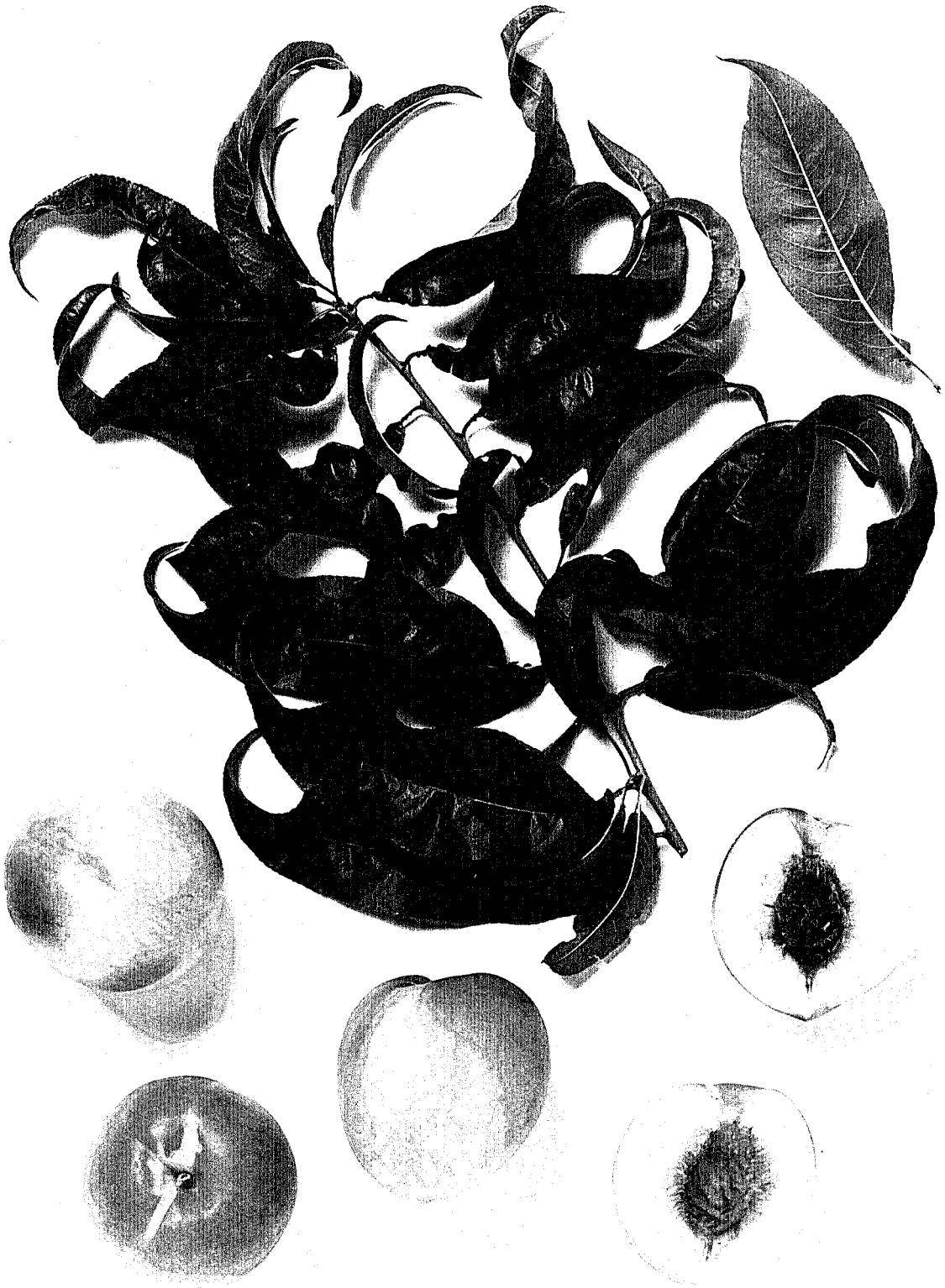

* * * * *